(12) United States Patent
Slater

(10) Patent No.: US 6,831,739 B2
(45) Date of Patent: Dec. 14, 2004

(54) COMPRESSION-BONDED PROBE WINDOW

(75) Inventor: Joseph B. Slater, Dexter, MI (US)

(73) Assignee: Kaiser Optical Systems, Ann Arbor, MI (US)

(*) Notice: Subject to any disclaimer, the term of this patent is extended or adjusted under 35 U.S.C. 154(b) by 141 days.

(21) Appl. No.: 10/350,525

(22) Filed: Jan. 24, 2003

(65) Prior Publication Data

US 2003/0142304 A1 Jul. 31, 2003

Related U.S. Application Data

(60) Provisional application No. 60/351,703, filed on Jan. 25, 2002.

(51) Int. Cl.[7] ............... G01J 3/02; G01J 3/44; G01N 21/64
(52) U.S. Cl. .............. 356/300; 356/301; 356/317; 250/458.1
(58) Field of Search .............. 356/300, 301, 356/317, 318, 417, 241.5, 241.1; 359/894, 895; 250/458.1, 459.1, 461.1, 461.2

(56) References Cited

U.S. PATENT DOCUMENTS

| | | | | |
|---|---|---|---|---|
| 4,573,761 A | * | 3/1986 | McLachlan et al. | 356/301 |
| 5,377,004 A | | 12/1994 | Owen et al. | 356/301 |
| 5,953,477 A | | 9/1999 | Wach et al. | 385/115 |
| 5,974,211 A | | 10/1999 | Slater | 385/33 |
| 5,978,534 A | | 11/1999 | O'Rourke et al. | 385/52 |
| 6,144,791 A | | 11/2000 | Wach et al. | 385/123 |
| 6,174,424 B1 | | 1/2001 | Wach et al. | 205/73 |
| 6,222,970 B1 | | 4/2001 | Wach et al. | 385/115 |
| 6,246,479 B1 | | 6/2001 | Jung et al. | 356/419 |
| 6,249,348 B1 | | 6/2001 | Jung et al. | 356/419 |
| 6,292,610 B1 | | 9/2001 | O'Rourke et al. | 385/52 |
| 6,362,888 B1 | | 3/2002 | Jung et al. | 356/419 |
| 6,366,726 B1 | | 4/2002 | Wach et al. | 385/115 |
| 6,370,406 B1 | | 4/2002 | Wach et al. | 600/310 |
| 6,373,573 B1 | | 4/2002 | Jung et al. | 356/419 |
| 6,416,234 B1 | | 7/2002 | Wach et al. | 385/70 |
| 6,483,581 B1 | | 11/2002 | Ben-Amotz et al. | 356/301 |
| 6,487,349 B2 | | 11/2002 | Wach et al. | 385/115 |
| 6,519,037 B2 | | 2/2003 | Jung et al. | 356/419 |
| 2001/0043330 A1 | | 11/2001 | Jung et al. | 356/419 |
| 2001/0055113 A1 | | 12/2001 | Yin | 356/301 |
| 2003/0016359 A1 | | 1/2003 | Jung et al. | 356/419 |

\* cited by examiner

*Primary Examiner*—F. L Evans
(74) *Attorney, Agent, or Firm*—Gifford, Krass, Groh, Sprinkle, Anderson & Cikowski, PC

(57) ABSTRACT

In an optical measurement probe of the type which incorporates a window configuration suited to on-line process control and other applications this invention provides an improved technique for bonding such a window to probe body or process vessel. In general terms, the improvement arises through the use of a compression ring around the bonding area to maintain a consistent seal. In terms of apparatus, a hollow probe body terminates in a distal end having a flanged portion with an inner and outer wall that extends back into the body. The outer wall of the window is sealed against the inner wall of the flanged portion, with compression material urged against the outer wall of the flanged portion to pressurize the seal between the window and the inner wall of the flanged portion. In the preferred embodiment, the compression material is ring-shaped and exhibits substantially the same thermal expansion coefficient as the window. In the case where a sapphire window is used, titanium or Invar may be used for the compression material. The window may be generally cylindrical though, in the preferred embodiments, cork-shaped or spherical window are used.

7 Claims, 2 Drawing Sheets

COMPRESSION-BONDED PROBE WINDOW

REFERENCE TO RELATED APPLICATION

This application claims priority from U.S. Provisional Patent Application Ser. No. 60/351,703, filed Jan. 25, 2002, the entire content of which is incorporated herein by reference.

FIELD OF THE INVENTION

This invention relates generally to optical measurement probes and, in particular, to probes which utilize a window configuration suited to on-line process control and other applications and, more particularly, to an improved technique for bonding such a window to probe body or process vessel.

BACKGROUND OF THE INVENTION

Optical characterization techniques based upon the Raman effect and fluorescence have become important tools in process monitoring and control for industries involved with hazardous materials, pharmaceuticals, and so forth. In such applications, it is typical for probe having a sealed window to be introduced into the process flow, making remote connection to analytical equipment through optical fibers, for example.

Current immersion window designs used by spectroscopic analysis systems rely on several techniques for sealing the window to the probe body. The two most broad categories are elastomeric seals, which include O-rings, gaskets, adhesive, etc., and metal seals. Metal seals can be subdivided into soft solder, metal spring seals and compression bonding. In general, metal seals are the most desirable type, offering the potential of high temperature resistance, high-pressure resistance, hermetic sealing, longevity and robustness.

The brazed window seal is the most common in the spectroscopic probe industry. Shown in FIG. 1, this arrangement consists of a window 102, typically sapphire, which is brazed to the surrounding probe body 104, typically with gold or a gold alloy 106. This technique has all the advantages of metal seals listed above, plus the fact that the sealing is done to the edge of the window thus leaving the surface flush to the outside of the probe without any special forming of the window itself. The disadvantages of this approach are that thermal shocks, particularly those proceeding from cold to hot, can create large tensile stresses and crack the window. In addition, these window assemblies are expensive and time-consuming to construct.

An alternative to the brazed window is the compression bonded window shown in FIG. 2. In this case, the window 202 is tapered and is pressed into the probe body 204. The interface may or may not have a ductile metal, such as gold, to aid in the sealing. This approach is inexpensive and quick, but has the disadvantage of losing compression on the window as the probe body expands at high temperature.

SUMMARY OF THE INVENTION

In an optical measurement probe of the type which incorporates a window configuration suited to on-line process control and other applications this invention provides an improved technique for bonding such a window to probe body or process vessel. In general terms, the improvement arises through the use of a compression ring around the bonding area to maintain a consistent seal.

In terms of apparatus, a hollow probe body terminates in a distal end having a flanged portion with an inner and outer wall that preferably extends back into the body. The outer wall of the window is sealed against the inner wall of the flanged portion, with compression material urged against the outer wall of the flanged portion to pressurize the seal between the window and the inner wall of the flanged portion.

In the preferred embodiment, the compression material is ring-shaped and exhibits substantially the same thermal expansion coefficient as the window. In the case where a sapphire window is used, titanium or Invar may be used for the compression material. Invar is well know to those of skill in mechanical design as an alloy of iron and nickel, plus other elements such as silicon and manganese, to achieve a very low coefficient of thermal expansion. The window may be generally cylindrical though, in the preferred embodiments, cork-shaped or spherical window are used.

DETAILED DESCRIPTION OF THE INVENTION

Figure 1:
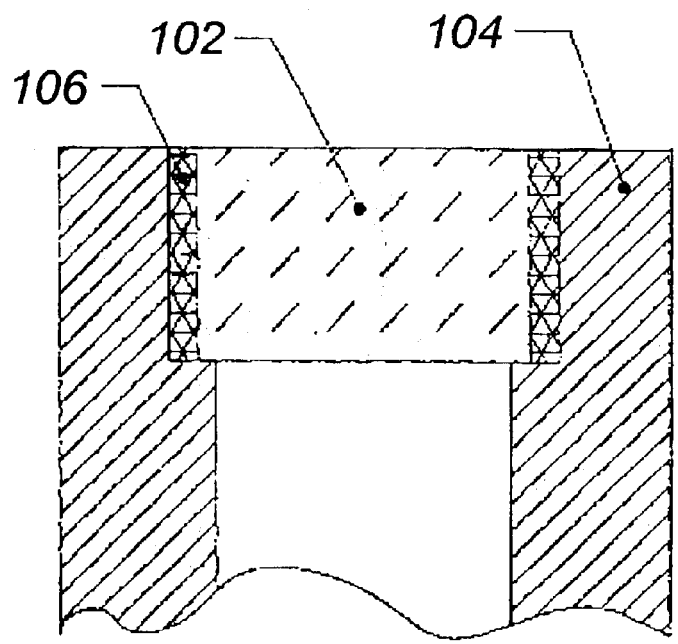
FIG. 1 illustrates a prior art bonding technique wherein a window, typically sapphire, is brazed to a surrounding probe body, typically with gold or a gold alloy.
Figure 2:
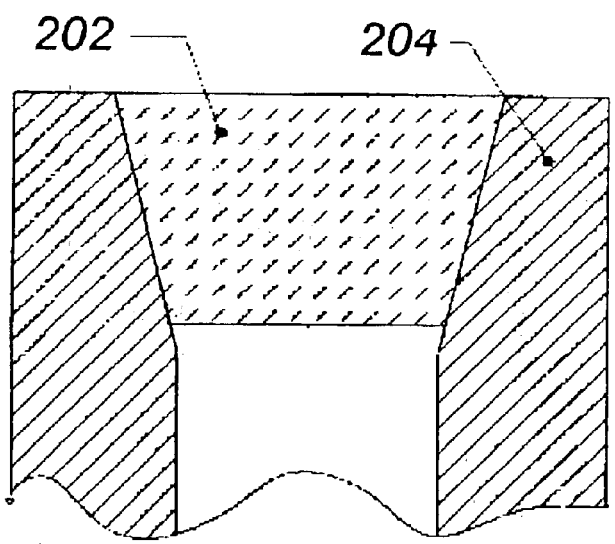
FIG. 2 illustrates a different prior-art technique wherein a tapered window is pressed into a probe body.
Figure 3:
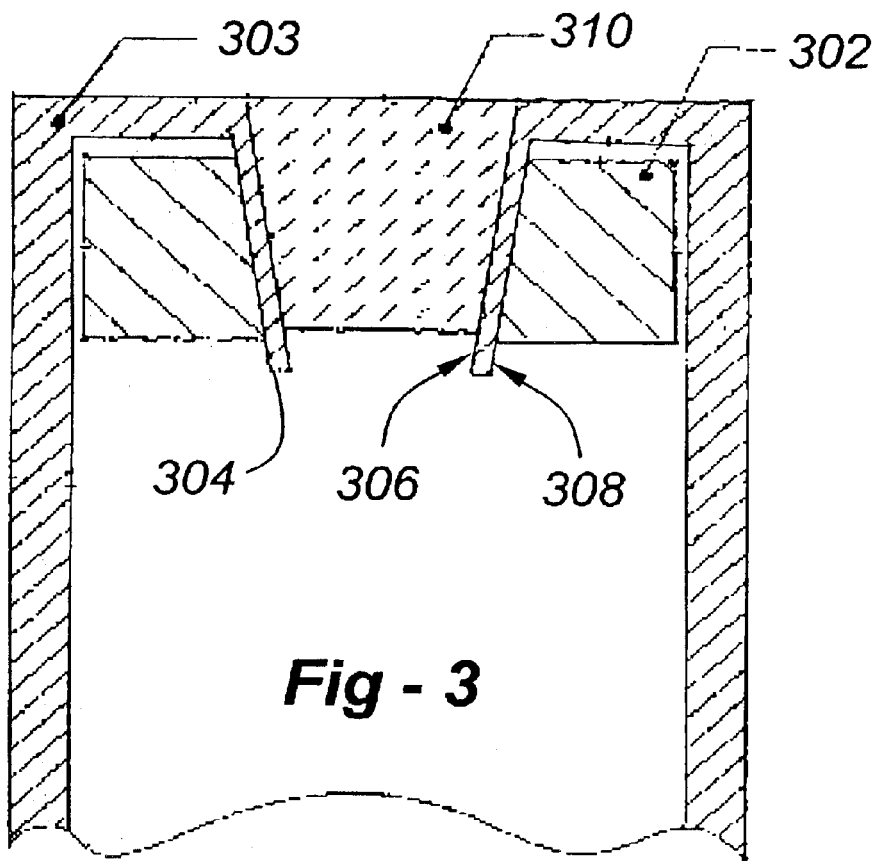
FIG. 3 is a diagram that illustrates an improved compression bonding approach according to the invention which adds an additional compression ring around the bonding area.

This invention improves upon existing compression-bonding approaches through the addition of a compression ring 302 around the bonding area, as shown in FIG. 3. In the preferred embodiment, the distal end of the probe body 303 includes an inwardly directed flange 304 having an inner wall 306 and an outer wall 308. The window 310 has an outer wall which makes intimate contact with the inner wall 306, such that the pressure applied by the ring 302 maintains a tight seal.

In the preferred embodiment, the compression ring has the same thermal expansion coefficient as the window (titanium or Invar would be potential candidate metals), and thus would maintain compression on the seal over extended temperature ranges.

Figure 4:
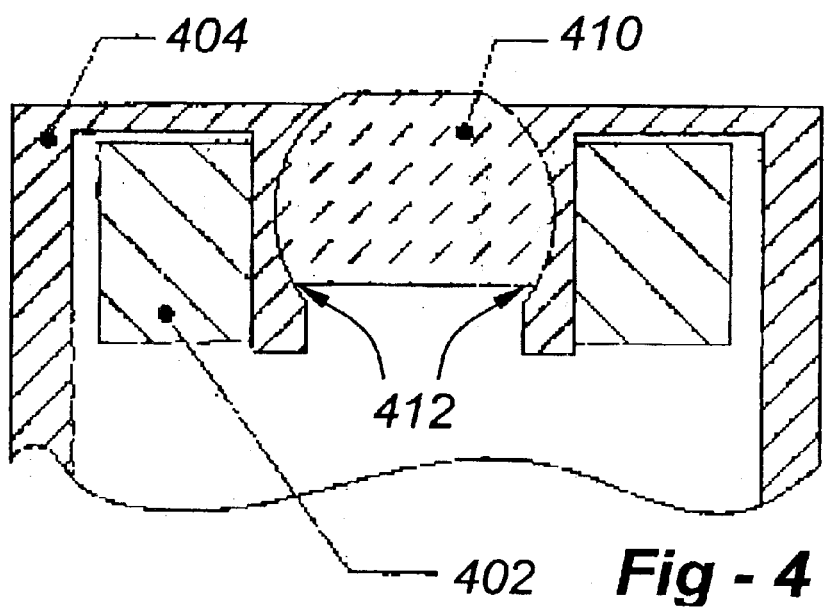
FIG. 4 shows an alternative embodiment utilizing a window having a domed or spherical wall.

An alternative embodiment, shown in FIG. 4, utilizes a window 410 having a domed or spherical wall. Such a window could, for example, start as a ball lens and have polished flats on opposite sides. This window is pressed into a spherical recess 412. The compression ring 402 would again be used to squeeze the walls of the recess so as to seal the window to the probe body 404. The recess could extend slightly beyond the equator of the spherical walled window and thus be captured, providing an additional benefit relative to the tapered window of FIG. 3.

I claim:

1. A sealed probe, comprising:
   a probe body terminating in a distal end having a flanged portion with an inner and outer wall;
   a window having an outer wall sealed against the inner wall of the flanged portion; and
   compression material urged against the outer wall of the flanged portion operative to pressurize the seal between the window and the inner wall of the flanged portion.

2. The sealed probe of claim 1, wherein the compression material has substantially the same thermal expansion coefficient as the window.

3. The sealed probe of claim 1, wherein the window is a sapphire window.

4. The sealed probe of claim 3, wherein the compression material is titanium.

5. The sealed probe of claim 3, wherein the compression material is Invar.

6. The sealed probe of claim 1, wherein the compression material is in the form of a circular ring.

7. The sealed probe of claim 1, wherein the outer wall of the window is generally spherical.

* * * * *